United States Patent [19]
Vevert et al.

[11] Patent Number: 4,839,358
[45] Date of Patent: Jun. 13, 1989

[54] ALPHA-MERCAPTOMETHYL-BENZENE PROPANAMIDES, PHARMACEUTICAL COMPOSITIONS AND USE

[75] Inventors: Jean-Paul Vevert, Pantin; Francoise Delevallee, Fontenay-sous-Bois; Jean-Claude Gasc; Francis Petit, both of Bondy, all of France

[73] Assignee: Roussel Uclaf, Paris, France

[21] Appl. No.: 159,265

[22] Filed: Feb. 23, 1988

[30] Foreign Application Priority Data

Feb. 26, 1987 [FR] France ................... 87 02546

[51] Int. Cl.$^4$ ............... A61K 31/40; A61K 31/535; C07D 295/22
[52] U.S. Cl. ................. 514/237.8; 514/212; 514/227.5; 514/255; 540/606; 544/58.1; 544/159; 544/382; 546/224; 548/557
[58] Field of Search ............. 540/606; 544/58.1, 159, 544/382; 546/224; 548/557; 514/212, 227.5, 237.8, 255

[56] References Cited

U.S. PATENT DOCUMENTS 4,216,160 8/1980 Dorn et al. ................... 564/192
4,263,293 4/1981 Sundeen et al. ............... 544/159

Primary Examiner—Robert W. Ramsuer
Attorney, Agent, or Firm—Bierman and Muserlian

[57] ABSTRACT

Novel α-mercaptomethyl-benzene propanamides of the formula

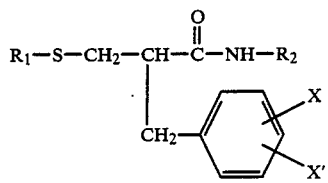

wherein $R_1$ is selected from the group consisting of hydrogen and

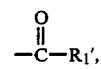

$R_1'$ is selected from the group consisting of alkyl of 1 to 5 carbon atoms and aryl optionally substituted with at least one member of the group consisting of —OH, —NO$_2$, halogen and alkyl and alkoxy of 1 to 5 carbon atoms, X and X' are individually selected from the group consisting of hydrogen, alkyl and alkoxy of 1 to 5 carbon atoms, —OH, halogen and —CF$_3$, R$_2$ is selected from the group consisting of pyrrolidinyl, morpholinyl, piperidinyl, piperazinyl, tetrahydrothiazinyl and hexahydroazepinyl, all optionally substituted with at least one member of the group consisting of alkyl and alkoxy of 1 to 5 carbon atoms, —OH, —NO$_2$, —CF$_3$, halogen and acyl of an organic carboxylic acid of 1 to 7 carbon atoms and their non-toxic, pharmaceutically acceptable acid addition salts having analgesic activity, antidepression and anxiolytic properties.

18 Claims, No Drawings

ALPHA-MERCAPTOMETHYL-BENZENE PROPANAMIDES, PHARMACEUTICAL COMPOSITIONS AND USE

STATE OF THE ART

Related compounds are described in European Pat. No. 0,137,746 and commonly assigned U.S. patent application Ser. No. 715,634 filed Mar. 25, 1985.

OBJECTS OF THE INVENTION

It is an object of the invention to provide the novel compounds of formula I and their non-toxic, pharmaceutically acceptable acid addition salts and their preparation.

It is another object of the invention to provide novel analgesic and other pharmaceutical compositions and a novel method of relieving pain in warm-blooded animals.

These and other objects and advantages of the invention will become obvious from the following detailed description.

THE INVENTION

The novel compounds of the invention are selected from the group consisting of α-mercaptomethyl-benzene propanamides of the formula

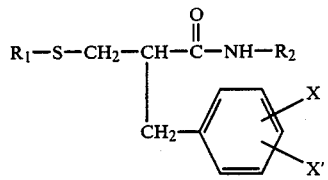

wherein $R_1$ is selected from the group consisting of hydrogen and

$R_1'$ is selected from the group consisting of alkyl of 1 to 5 carbon atoms and aryl optionally substituted with at least one member of the group consisting of —OH, —NO$_2$, halogen and alkyl and alkoxy of 1 to 5 carbon atoms, X and X' are individually selected from the group consisting of hydrogen, alkyl and alkoxy of 1 to 5 carbon atoms, —OH, halogen and —CF$_3$, $R_2$ is selected from the group consisting of pyrrolidinyl, morpholinyl, piperidinyl, piperazinyl, tetrahydrothiazinyl and hexahydroazepinyl, all optionally substituted with at least one member of the group consisting of alkyl and alkoxy of 1 to 5 carbon atoms, —OH, —NO$_2$, —CF$_3$, halogen and acyl of an organic carboxylic acid of 1 to 7 carbon atoms and their non-toxic, pharmaceutically acceptable acid addition salts.

Examples of alkyl of 1 to 5 carbon atoms are methyl, ethyl, n-propyl, isopropyl, n-butyl, isobutyl, tert-butyl and n-pentyl. Examples of alkoxy of 1 to 5 carbon atoms are methoxy, ethoxy, n-propoxy, isopropoxy, n-iso- or tert-butoxy. The halogen may be fluorine, chlorine, bromine, or iodine.

When $R_1$ is

$R_1'$ is preferably methyl or ethyl. When $R_1'$ is aryl, it is preferably a phenyl. When $R_1'$ is a substituted aryl, it is preferably aryl substituted by a member chosen from the group consisting of hydroxyl, methyl, ethyl, methoxy, ethoxy, nitro and chlorine.

X and X' individually are preferably hydrogen, methyl, ethyl, methoxy or ethoxy, chlorine, hydroxy or trifluoromethyl.

When $R_2$ is substituted, it is preferably a single substitutent, preferably selected from the group consisting of methyl, ethyl, methoxy, ethoxy, chlorine, hydroxy, nitro and trifluoromethyl and particularly N-acetyl.

The non-toxic, pharmaceutically acceptable addition salts with mineral or organic acids may be, for example, the salts formed with the following acids: hydrochloric acid, hydrobromic acid, nitric acid, sulfuric acid, phosphoric acid, acetic acid, formic acid, propionic acid, maleic acid, fumaric acid, succinic acid, tartaric acid, citric acid, oxalic acid, glyoxylic acid, aspartic acid, alkanesulfonic acids such as methane- and ethane- sulfonic acid, arylsulfonic acids such as benzene and p-toluenesulfonic acid and arylcarboxylic acids such as benzoic acids.

Among the preferred compounds of formula I are those wherein $R_1$ is hydrogen, those wherein $R_1$ is acetyl and those wherein $R_2$ is morpholinyl or pyrrolidinyl and their non-toxic, pharmaceutically acceptable acid addition salts. Particularly preferred is α-mercaptomethyl-N-(4-morpholinyl)benzene-propanamide and its acid addition salts.

The novel process of the invention for the preparation of the compounds of formula I comprises reacting an activated form of an acid of the formula

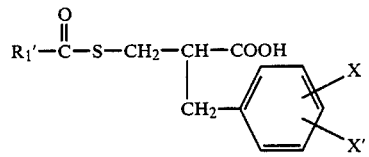

wherein $R_1'$, X and X' have the above definitions with an amine of the formula $R_2$—NH$_2$ where $R_2$ has the above definition to obtain a compound of formula I, optionally saponifying the latter to obtain the corresponding compound of formula I wherein $R_1$ is hydrogen and optionally salifying the compounds of formula I with an acid to form the acid addition salt.

The activation of the carboxyl of the compound of formula II for the condensation with the amine is preferably effected in the form of an acid chloride in the presence of dicyclohexylcarbodiimide in a solvent such as ether, tetrahydrofuran or a chlorinated solvent such as methylene chloride, 1,1-dichloroethane, chloroform or carbon tetrachloride.

Another process for the preparation of compounds of formula I comprises reacting an acid of the formula

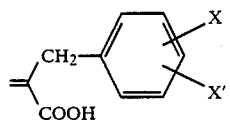

III or a functional derivative thereof with an amine of the formula NH$_2$—R$_3$ wherein R$_3$ has the definition of R$_2$ or R$_{2p}$ which is R$_2$ with protected reactive groups to obtain a compound of the formula

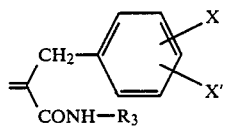

VI wherein X, X' and R$_3$ have the above definitions, subjecting the latter when R$_3$ is R$_{2p}$ to a deprotection agent to obtain a compound of the formula

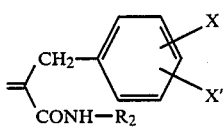

IV' reacting the latter with a thioacid of the formula

wherein R$_1$' has the above definition to obtain a compound of formula I wherein R$_1$ is

optionally saponifying the latter to obtain a compound of formula I wherein R$_1$ is hydrogen and optionally salifying the compounds of formula I to form the said addition salt.

In a preferred mode of the said process, a functional derivative of the acid of formula III such as the acid chloride is used and the reaction with the amine NH$_2$—R$_3$ is carried out wherein the indicated conditions for the reaction of the products of formula II with the amine NH$_2$—R$_2$; the protector group of the reactive functions of R$_2$ is chosen from the standard protector groups known to an expert. Examples are alkoxycarbonyl such as tert-butoxycarbonyl, cycloalkoxycarbonyl, and aralkoxycarbonyl; the possible deprotection of the product of formula IV can be carried out by acid hydrolysis, for example, with trifluoroacetic acid but other mineral or organic acids may be used. The thioacid reacted with the product of formula IV' is preferably thioacetic acid; and the saponification of the products of formula I in which R$_1$ is

is carried out particularly with alkali metal hydroxide. In certain cases, the action of the thioacid on the product of formula IV' can also lead to a substitution at R$_2$, particularly on a nitrogen atom. The product so obtained is then a product of formula I in which R$_1$ is

and R$_2$ is a heterocycle whose nitrogen atom is substituted by

The analgesic compositions of the invention are comprised of an analgesically effective amount of at least one compound of formula I and their non-toxic, pharmaceutically acceptable acid addition salts and an inert pharmaceutical carrier or excipient. The compositions may be in the form of tablets, dragees, capsules, granules, suppositories, injectable solutions or suspensions, ointments, creams, gels and aerosol preparations.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have very interesting enkephalinase inhibiting properties, and are endowed with a very good analgesic activity. They present also psychotrope properties, especially anti-depressive and anxiolytic properties.

Enkephalinase is a dipeptidylcarboxypeptidase which specifically hydrolyses the enkephaline methionine and leucine between the 3rd and 4th amino acid, thus liberating a tripep tide Tyr-Gly-Gly (Swerts, J. P., Perdrisot, R., Patey, G., de la Baume, S, and Schwartz, J. C., Europ. J. Pharmacol. (1979), 57, 279). Enkephalinase thus participates directly in the physiological degradation of the enkephalines which are natural endogenic ligands of the opiated receptors. The compounds of the invention, which retard the degradation of the enkephalines, therefore stimulate the defense reactions of the organisms against pain.

The compositions are useful in the treatment of muscular, articular or nervous pains, or rheumatic affections, of dental pains, of shingles and of migraine, as well as in the treatment of inflammatory diseases, notably of arthrosis, of lumbago and also by way of complementary treatment in infectious and febrile states. They can also be used to treat states of depression. The preferred compositions contain either α-mercapto-methyl-N-(4-morpholinyl)-benzene propanamide or α-mercaptomethyl-N-(1-pyrrolidinyl)-benzene propanamide and their non-toxic, pharmaceutically acceptable acid addition salts.

The novel method of the invention of relieving pain in warm-blooded animals, including humans, comprises administering to warm-blooded animals an analgesically effective amount of at least one compound of formula I and their non-toxic, pharmaceutically acceptable acid addition salts. The compositions may be administered orally, rectally, parenterally or topically to the skin or mucosa. The usual daily dose is 0.25 to 25 mg/kg depending on the condition treated, the specific compound and the method of administration.

The starting compounds of formula II may be prepared by the process of U.S. Pat. No. 4,053,651.

In the following examples there are described several preferred embodiments to illustrate the invention. However, it is to be understood that the invention is not intended to be limited to the specific embodiments.

EXAMPLE 1

α-[(acetylthio)-methyl]-N-(4-morpholinyl)-benzene propanamide

A solution of 41.3 g of α-(acetylthiomethyl)-benzene propanoyl chloride (Example 1 of French Patent No. 2,540,495) in 300 ml of methylene chloride was added dropwise at −10° C. to a solution of 33 g of N-aminomorpholine in 500 ml of methylene chloride. The aminomorpholine hydrochloride precipitated and after leaving the reaction mixture at ambient temperature overnight, the aminomorpholine hydrochloride was eliminated and the methylene chloride was evaporated under reduced pressure. The residue was stirred for 30 minutes in 300 ml of ether, then filtered and dried under reduced pressure to obtain 44.7 g of the expected product (86% yield) which had an Rf of 0.23 in chromatography on silica (eluent: ethyl acetate-methylene chloride, 50-50).

EXAMPLE 2

α-mercaptomethyl-N-(4-morpholinyl)-benzene propanamide 2.67 g of the product of Examaple 1 were dissolved in 166 ml of methanol cooled to −10° C. and 82.8 ml of 0.1N sodium hydroxide were added over 45 minutes. The temperature was allowed to return to 0° C. over 2 hours and 82.8 ml of 0.1N hydrochloric acid were added over 30 minutes followed by concentration to dryness under reduced pressure at 25° C. The residue was poured into the same volume of water and extraction was done with methylene chloride. The extracts were dried, filtered, concentrated and dried under reduced pressure to obtain 2.36 g of crude product which was purified by chromatography on silica (eluent:ethyl acetate 50 - methylene chloride 50 - MeOH 4) resulting in 1.61 g of the expected product melting at 110° C.

EXAMPLE 3

α-[(acetylthio)-methyl)]-N-(1-piperidinyl)-benzene propanamide

A solution of 5.135 g of α-(acethylthiomethyl) benzene propanoyl chloride in 40 ml of methylene chloride was added dropwise at −10° C. to a solution of 4.01 g of N-aminopiperidine in 60 ml of methylene chloride. The aminopiperidine hydrochloride precipitated and the reaction mixture stood at ambient temperature overnight. Then, the aminopiperidine hydrochloride was eliminated and the methylene chloride was evaporated off under reduced pressure. The residue was stirred for 30 minutes in 50 ml of ether and then was filtered. The product was dried under reduced pressure to obtain 6.85 g of product in the form of an oil which was purified by chromatography on silica (eluent:methylene chloride - ethyl acetate 98-2) to obtain 3.7 g of the expected product melting at 97° C.

EXAMPLE 4

α-mercaptomethyl-N-(1-piperidinyl) benzene propanamide

Using the procedure of Example 2, 3.4 g of the product of Example 3 dissolved in 215 ml of methanol, 106.1 ml of 0.1N sodium hydroxide and 106.1 ml of 0.1N hydrochloric acid were reacted to obtain 2.56 g of the expected product. After purification by chromatography on silica (eluent:ethyl acetate-methylene chloride, 12-88), the product melted at 119° C.

EXAMPLE 5

α-[(acetylthio)-methyl]-2,6-dichloro-N-(4-morpholinyl)-benzene propanamide 117.9 g of α-(acetylthiomethyl)-2,6-dichlorobenzene-propanoyl acid chloride in solution in 400 ml of methylene chloride were cooled to 0° C. and stirred with 6.65 ml of N-methylmorpholine and then with a solution of 5.9 ml of aminomorpholine in 200 ml of methylene chloride. The mixture was stirred for 18 hours while allowing the temperature to return to the ambient, and was then washed with water, dried, and the solvents were eliminated under reduced pressure. After chromatographing the residue on silica (eluent - methylene chloride - methanol, 100-1.5), then crystallizing from a mixture of ether and methylene chloride 8-2, 12 g of the expected product melting at 175° C. were obtained.

Preparation of α-(acetylthiomethyl)-2,6-dichlorobenzene propanoyl acid chloride

Step A: Methyl 2,6-dichloro α-(dimethylaminomethyl)-benzene propanoate

Under an inert atmosphere, 16 ml of diisopropylamine were added to 250 ml of tetrahydrofuran, and the mixture was cooled to −78° C., 65 ml of butyllithium were added dropwise followed by a solution of 12.4 g of methyl 3-(dimethylamino)-propanoate in 50 ml of tetrahydrofuran. After keeping the mixture at −78° C. for 30 minutes, 18.1 ml of hexamethylphosphotriamide were added dropwise. The temperature was allowed to return to ambient with stirring for 2 hours. Then, 500 ml of a saturated aqueous solution of ammonium chloride were added after which the solvents were eliminated under reduced pressure. The aqueous phase was extracted with ether and the solvent was eliminated under reduced pressure to obtain 28.8 g of the expected product.

Step B: [3-(2,6-dichlorophenyl)-2-methoxycarbonylpropyl]-trimethyl-ammonium iodide Under an inert atmosphere, a solution of 28.8 g of the ester of Step A in 140 ml of acetone was cooled to 0° C. and 100 ml of methyl iodide were added. The temperature was allowed to return to the ambient with stirring for 2 hours, followed by filtering the precipitate, washing it with ether and drying it under reduced pressure to obtain 53.3 g of the expected product.

Step C: 2,6-dichloro-α-methylenebenzene propanoic acid

Under an inert atmosphere, 120 ml of 2N sodium hydroxide were added to 53.3 g of the product of Step B in suspension in 500 ml of methanol. After refluxing the mixture for 2 hours, the solvents were eliminated under reduced pressure, and the residual aqueous phase was extracted with ether. After acidifying with 5N hydrochloric acid, extraction was done again with ether and then with ethyl acetate. The combined organic phases were dried, and the solvents were eliminated under reduced pressure to obtain 32 g of crude product which was crystallized from hexane and then melted at 132° C.

Step D: α-[(acetylthio)-methyl]-2,6-dichlorobenzene propanoyl chloride 30 ml of thioacetic acid were added to 12.7 g of the product of Step C in solution in 20 ml of methylene chloride and the mixture was stirred for 16 hours at ambient temperature. The solvent was eliminated under reduced pressure to obtain 17.2 g of the expected product.

EXAMPLE 6

2,6-dichloro-N-[4-morpholinyl]-α-mercaptomethyl benzene propanamide

Under an inert atmosphere, a solution of 1.7 g of the product of Example 5 in 400 ml of methanol was cooled to 0° C. and then over 15 minutes, 48 ml of 0.1N sodium hydroxide were added with stirring for 2 hours at 0° C. The reaction medium was neutralized with 5 ml of N hydrochloric acid, and the solvents were eliminated under reduced pressure at 30° C. The residual aqueous phase was extracted with methylene chloride and the combined organic phases were dried, and the solvents were eliminated under reduced pressure. After chromatography on silica (eluent:methylene chloride - methanol, 100-4), 1.30 g of the expected product melting at 142° C. were obtained.

EXAMPLE 7

α-[(acetylthio)-methyl]-N-(hexahydro-1H-azepinyl)-benzene propanamide

Using the procedure of Example 5, 2.56 g of α-(acetylthiomethyl)-benzene propanoyl chloride and 1.26 g of 1-amino-homo-piperidine were reacted to obtain after chromatography on silica (eluent:methylene chloride - methanol, 100-2), 2 g of the expected product melting at 126° C.

EXAMPLE 8

N-(hexahydro-1H-azepinyl)-α-(mercaptomethyl)-benzene propanamide

Using the procedure of Example 6, 2 g of the product of Example 7 and 62.8 ml of 0.1N sodium hydroxide were reacted to obtain after chromatography on silica (eluent:methylene chloride - methanol, 100-2), 1.7 g of the expected product melting at about 82° C.

EXAMPLE 9

α-[(acetylthio)-methyl]-N-(1-pyrrolidinyl)-benzene propanamide

Using the procedure of Example 5, 2.56 g of α-(acetylthiomethyl) benzene propanoyl chloride and 1.35 g of N-aminopyrrolidine hydrochloride while maintaining the reaction for 72 hours were reacted to obtain after chromatography and trituration of the residue in isopropyl ether, 0.77 g of the expected product melting at 91° C.

EXAMPLE 10

α-mercaptomethyl-N-(1-pyrrolidinyl)-benzene propanamide

Using the procedure of Example 6, 0.77 g of the product of Example 9 and 26 ml of 0.1N sodium hydroxide were reacted to obtain after chromatography on silica (eluent:methylene chloride - methanol, 100-3), 0.57 g of the expected product melting at 93° C.

EXAMPLE 11

α-[(acetylthio)-methyl]-N-(tetrahydro-2H-1,4-thiazin-4-yl)-benzene propanamide

Step A: 4-[(2-methylene-3-phenyl-propanoyl)-amino]-tetrahydro-2H-1,4-thiazine

Using the procedure of Example 5, 1.84 g of (2-methylene-3-phenyl)-propanoic acid chloride and 1.2 g of 4-amino-tetrahydro-2H-1,4-thiazine were reacted to obtain 1.8 g of the expected crude product which was purified by chromatography on silica, (eluent:methylene chloride - methanol, 100-1) so that it melted at 141° C.

Step B: α-[(acetylthio)-methyl]-N-(tetrahydro-2H-1,4-thiazin-4-yl)-benzene propanamide 0.6 g of the product of Step A was stirred for 24 hours at ambient temperature in 10 ml of thioacetic acid and the excess of acid was eliminated under an inert atmosphere at 40°-45° C. The residue was taken up on 200 ml of methylene chloride, washed with a sodium bicarbonate solution, dried and the solvent was eliminated under reduced pressure. The residue was taken up in isopropyl ether to obtain 0.72 g of the expected product melting at 138° C.

Preparation of 4-amino-tetrahydro-2H-1,4-thiazine

Step A: 4-nitroso-tetrahydro-2H-1,4-thiazine 16 g of thiomorpholine and 32 ml of hydrochloric acid were heated to 80°/85° C. in 120 ml of water and over 1 hour, there were added a solution of 5 g of sodium nitrite in 60 ml of water with stirring for 5 hours at 80° C. After allowing the mixture to return to ambient temperature and maintaining stirring for 12 hours, the reaction medium was alkalized with an aqueous solution of 4N potassium hydroxide, then extracted with methylene chloride. The organic phase was washed with salted water, dried and the solvents were eliminated under reduced pressure to obtain 14 g of the expected product melting at or less than 50° C.

Step B: 4-amino-tetrahydro-2H-1,4-thiazine 5.9 g of the product of Step A in solution in 50 ml of hydrochloric acid were cooled to −10° C. and then over 1 hours and a half, 14.6 g of powdered zinc were added. The reaction medium was cooled to −20° C. for 12 hours and then allowed to return to ambient temperature. The mixture was poured into water and a saturated aqueous solution of sodium bicarbonate was added. After filtering, the filtrate was extracted with methylene chloride and ethyl acetate and the combined organic phases were dried, and the solvents were eliminated under reduced pressure. After chromatography of the rsidue on silica (eluent:methylene chloride - methanol, 100-7) 2.2 g of the expected product were obtained.

EXAMPLE 12

α-mercaptomethyl-N-(tetrahydro-2H-1,4,-thiazin-4-yl)-benzene propanamide

Using the procedure of Example 6, 0.72 g of the product of Example 11 and 22 ml of 0.1N sodium hydroxide were reacted to obtain after chromatographyl on silica (eluent:methylene chloride - methanol, 100/2), 0.56 g of the expected product melting at 120° C.

EXAMPLE 13

α-[(acetylthio)-methyl]-N-[4-acetyl-(1-piperazinyl)-benzene]propanamide

Step A: Tertbutyl 4-[(2-benzyl-1-oxo-2-propenyl)-amino]-1-piperazine carboxylate Using the procedure of Example 5, 4.54 g of (2-methylene-3-phenyl)-propanoic acid chloride and 3.28 g of tertbutyl 4-amino-1-piperazine carboxylate in solution in 100 ml of methylene chloride which was added at −10° C. over 20 minutes were reacted. After eliminating the solvents under reduced pressure, the residue was taken up in isopropyl ether and after drying, 7.4 g of the expected product melting at 160° C. were obtained.

Step B: α-methylene-N-(1-piperazinyl)-benzene propanamide

Under an inert atmosphere, 7.4 g of the product of Step A were cooled to −15° C. in 20 ml of methylene chloride and then 13 ml of trifluoroacetic acid were added dropwise. After allowing to return to ambient temperature and stirring for 2 hours, neutralizing with a saturated aqueous solution of sodium bicarbonate, extractin was done with ethyl acetate. The extracts were washed with salted water, dried and the solvents were eliminated under reduced pressure to obtain 3.6 g of the expected product melting at 78° C.

Step C: α-[(acetylthio)-methyl]-N-[4-acetyl-(1-piperazinyl)]-benzene propanamide 1.8 g of the product of Step B were stirred for 72 hours in 20 ml of thioacetic acid, then concentrated under an inert atmosphere. The residue was taken up in 200 ml of methylene chloride, wasshed with saturated aqueous solution of sodium bicarbonate, dried, and the solvent was eliminated under reduced pressure. The residue was chromatographed on silica (eluent:methylene chloride - methanol, 100/3), to obtain 2.05 g of the expected product.

Tertbutyl-4-amino-1-piperazine carboxylate

Step A: Tertbutyl bis-(2-chloroethyl)-carbamate 17.2 g of bis-chloroethylamine hydrochloride in 400 ml of acetonitrile were cooled to 0° C. and 14 ml of triethylamine were added. Then, over 20 minutes, 24.5 ml of ditertbutoxydicarbonate in solution in 100 ml of acetonitrile were added. The temperature was allowed to return to the ambient, and the reaction medium was stirred for 16 hours and then filtered. The filtrate was concentrated under reduced pressure and the residue was taken up in ether, filtered again and the solvent was expelled. The oily residue was distilled under reduced pressure ($10^{-1}$ mbar) at 80° C. to obtain 18 g of the expected product.

Step B: Tertbutyl 4-amino-1-piperazine carboxylate

Under an inert atmosphere at ambient temperature, 15.3 g of the product of Step A and 80 ml of hydrazine hydrate were mixed together and then 150 ml of a saturated aqueous solution of ammonium chloride were added. Extraction was done with methylene chloride and the organic phase was washed with an aqueous solution of ammonium chloride, dried, and the solvent was eliminated under reduced pressure. After chromatography on silica (eluent:methylene chloride - methanol, 100/7) 5 g of the expected product were obtained.

EXAMPLE 14

N-[4-acetyl-(1-piperazinyl)-α-mercaptomethyl]-benzene propanamide

Using the procedure of Example 6, 1.75 g of the product of Example 13 and 60 ml of 0.1N sodium hydroxide were reacted to obtain after chromatography on silica (eluent:methylene chloride - methanol, 100/4), 1.5 g of the expected product melting at about 50° C.

| Analysis: $C_{16}H_{23}O_2N_3S$: molecular weight = 321.426 | | | | |
|---|---|---|---|---|
| | % C | % H | % N | % S |
| Calculated: | 59.8 | 7.2 | 13.1 | 10.0 |
| Found: | 60.1 | 7.3 | 13.0 | 9.8 |

EXAMPLE 15

Tablets were prepared containing 50 mg of the compound of Example 2 and sufficient excipient of starch, lactose, talc and magnesium stearate for a final tablet weight of 350 mg.

PHARMACOLOGICAL STUDY

A. Determination of the Inhibiting Effect of Enkephalinase

The activity of enkephalinase was determined starting with a piece of renal membrane of a rat. The kidneys were removed on ice and homogenized in HEPES 0.05M buffer pH 7.5 containing magnesium chloride (50 times the volume). After a first centrifuging at 1,500 g, the particular fraction was obtained after centrifuging at 15,000 g for 20 minutes. The residue was then washed and suspended in HEPES buffer and kept at −20 C. A part of this membrane preparation was placed in the presence of octyl β-D-glucopyranoside (50 mM in final centrifuging) for 15 minutes 15 4° C. After centrifuging at 100,000 g for one hour, the supernatant was removed and frozen by aliquots at −20° C. The concentration in proteins was determined by the method with Comassie blue.

An aliquot of the protein fraction so prepared was pre-incubated at 25° C. for 10 minutes in HEPES 0.05M buffer pH 7.5 or in the presence of the test product. The substrate added was a non-natural enkephaline of the formula succinyl-Ala-Ala-Phe-amino-methylcoumarine (reference 1) (40 μM in final concentration): the incubation was continued at 37° C. for 30 minutes. The reaction was stopped by heating to 95° C. for 5 minutes and each incubate was centrifuged. A solution of aminopeptidase M (4 μM in final concentration) and of thiorphan (reference 2) ($10^{-5}$M) was added to the supernatant and the mixture was taken to 37° C. for one hour. The reaction was stopped as previously described and the fluorescence of the 7-aminomethylcoumarine so produced was determined. The effect of the products under test was detemined by calculating the $IC_{50}$ as the concentration which inhibits the hydrolysis of the substrate by 50%.

Reference 1: R. A. Munford, P. A. Pierzchala, A-W. Strauss and M. Zimmerman.

Purification of a membrane-bound metalloendo peptidase from porcine kidney that degrades peptides hormones. Proc. Natl. Acad. Sci. 78, No. 11, p. 6623.

Reference 2: Enkephalinase inhibitor described in Example 20 of the French Pat. No. 2,480,747.

RESULTS

| Product of Example | $IC_{50}$ |
|---|---|
| 2 | $2.2.10^{-7}$M |
| 8 | $3.9.10^{-7}$M |
| 10 | $7.1.10^{-8}$M |
| 12 | $3.5.10^{-7}$M |

B. Study of the Analgesic Activity in Mice

Stretching Caused by Acetic Acid in Mice

The test used was based on the fact reported by R. KOSTER et al [Fed. Proc. (1959), Vol. 18, p. 412] in which the intraperitoneal injection of acetic acid caused in mice repeated stretching and twisting movements which can persist for more than 6 hours. The analgesics prevent or diminish this syndrome which can be considered as the exteriorization of a diffuse abdominal pain. A 1% solution of acetic acid in water was used, administered at a rate of 10 ml/kg. The product studied was administered by oral route half-an-hour before injection of the acetic acid, the mice being without food for a minimum 6 hours. The stretchings were observed and counted for each mouse for an observation period of 15 minutes. The results were expressed as the $AD_{50}$, that is to say, the active dose which enabled a reduction of 50% of the number of stretchings as compared with control animals. The $AD_{50}$ found for the compound of Example 2 was 80 mg/kg.

C. Test of Anti-depressive Activity

The tests were carried out on groups of 5 Sprague Dawley rats and the inexperienced animals were placed for 15 minutes in a vertical perspex cylinder (diameter: 18 cm, height: 40 cm) containing water at 25° C. to a height of 15 cm (initial swimming test). They were then dried for 15 minutes in an enclosure heated to 32° C. 24 hours later, they were replaced in the cylinder filled with water and the total duration of immobility was measured for 5 minutes. The compound was administered orally successively 24, 5 and 1 hour before the test. The first administration took place immediately after the initial swimming test, just before replacing the animals in their breeding box. The average of the groups treated were compared with those of the control group by the Dunnett test.

RESULTS

| Dose in mg/kg of product of Example 2 | Duration of immobility in seconds % variation |
|---|---|
| 0 | 232 ± 7 |
| 20 mg/kg × 3 | 138 ± 20* (−41) |

Various modifications of the products and method of the invention may be made without departing from the spirit or scope thereof and it is to be understood that the invention is intended to be limited only as defined in the appended claims.

What we claim is:

1. A compound selected from the group consisting of α-mercaptomethyl-benzene propanamides of the formula

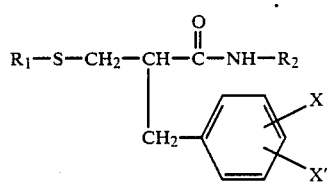

wherein $R_1$ is selected from the group consisting of hydrogen and

$R_1'$ is selected from the group consisting of alkyl of 1 to 5 carbon atoms and aryl optionally substituted with at least one member of the group consisting of —OH, —$NO_2$, halogen and alkyl and alkoxy of 1 to 5 carbon atoms, X and X' are individually selected from the group consisting of hydrogen, alkyl and alkoxy of 1 to 5 carbon atoms, —OH, halogen and —$CF_3$, $R_2$ is selected from the group consisting of pyrrolidinyl, morpholinyl piperidinyl, piperazinyl, tetrahydrothiazinyl and hexahydroazepinyl, all optionally substituted with at least one member of the group consisting of alkyl and alkoxy of 1 to 5 carbon atoms, —OH, —$NO_2$, —$CF_3$, halogen and acyl of an organic carboxylic acid of 1 to 7 carbon atoms and their non-toxic, pharmaceutically acceptable acid addition salts.

2. A compound of claim 1 wherein $R_1$ is hydrogen.

3. A compound of claim 1 whrein $R_1$ is acetyl.

4. A compound of claim 2 whrein $R_2$ is morpholinyl or pyrrolidinyl.

5. A compound of claim 3 wherein $R_2$ is morpholinyl or pyrrolidinyl.

6. A compound of claim 1 selected from the group consisting of α-mercaptomethyl-N-(4-morpholinyl)-benzene propanamide, and α-mercaptomethyl-N-(1-pyrrolidinyl)-benzene propanamide and their non-toxic, pharmaceutically acceptable acid addition salts.

7. An analgesic composition comprising an analgesically effective amount of at least one compound of claim 1 and an inert pharmaceutical carrier.

8. A composition of claim 7 wherein in the active compound $R_1$ is hydrogen.

9. A composition of claim 7 wherein in the active compound $R_1$ is acetyl.

10. A composition of claim 8 wherein in the active compound $R_2$ is morpholinyl or pyrrolidinyl.

11. A composition of claim 9 wherein in the active compound $R_2$ is morpholinyl or pyrrolidinyl.

12. A composition of claim 7 wherein the active compound is selected from the group consisting of α-mercaptomethyl-N-(4-morpholinyl)-benzene propanamide, and α-mercaptomethyl N-(1-pyrrolidinyl)-benzene propanamide, and their non-toxic, pharmaceutically acceptable acid addition salts.

13. A method of relieving pain in warm-blooded animals comprising administering to warm-blooded animals an analgesically effective amount of claim 1.

14. A method of claim 13 wherein in the active compound $R_1$ is hydrogen.

15. A method of claim 13 wherein in the active compound $R_1$ is acetyl.

16. A method of claim 14 wherein in the active compound $R_2$ is morpholinyl or pyrrolidinyl.

17. A method of claim 15 wherein in the active compound $R_2$ is morpholinyl or pyrrolidinyl.

18. A method of claim 13 wherein the active compound is selected from the group consisting of α-mercaptomethyl-N-(4-morpholinyl) benzene propanamide, and α-mercaptomethyl-N-(1-pyrrolidinyl) benzene propanamide, and their non-toxic, pharmaceutically acceptable acid addition salts.

* * * * *